(12) United States Patent
Amey

(10) Patent No.: US 7,973,174 B2
(45) Date of Patent: Jul. 5, 2011

(54) PROCESS OF MAKING 3-AMINOPENTANENITRILE

(75) Inventor: Ronald L. Amey, Wilmington, DE (US)

(73) Assignee: Invista North America S.A.R.L., Wilmington, DE (US)

( * ) Notice: Subject to any disclaimer, the term of this patent is extended or adjusted under 35 U.S.C. 154(b) by 520 days.

(21) Appl. No.: 12/090,440

(22) PCT Filed: Oct. 18, 2005

(86) PCT No.: PCT/US2005/037642
§ 371 (c)(1),
(2), (4) Date: Aug. 28, 2008

(87) PCT Pub. No.: WO2007/046799
PCT Pub. Date: Apr. 26, 2007

(65) Prior Publication Data
US 2009/0177004 A1    Jul. 9, 2009

(51) Int. Cl.
C07C 253/30    (2006.01)
C07C 255/07    (2006.01)

(52) U.S. Cl. .................................................. 548/452

(58) Field of Classification Search .................. None
See application file for complete search history.

(56) References Cited

U.S. PATENT DOCUMENTS

| | | |
|---|---|---|
| 2,768,132 A | 10/1956 | Halliwell |
| 3,370,082 A | 2/1968 | Eisfeld et al. |
| 3,496,215 A | 2/1970 | Drinkard et al. |
| 3,496,217 A | 2/1970 | Drinkard, Jr. et al. |
| 3,496,218 A | 2/1970 | Drinkard, Jr. |
| 3,522,288 A | 7/1970 | Drinkard, Jr. et al. |
| 3,536,748 A | 10/1970 | Drinkard, Jr. et al. |
| 3,551,474 A | 12/1970 | Drinkard et al. |
| 3,564,040 A | 2/1971 | Downing et al. |
| 3,579,560 A | 5/1971 | Drinkard et al. |
| 3,655,723 A | 4/1972 | Drinkard, Jr. et al. |
| 3,694,485 A | 9/1972 | Drinkard, Jr. et al. |
| 3,752,839 A | 8/1973 | Drinkard, Jr. et al. |
| 3,766,231 A | 10/1973 | Gosser et al. |
| 3,766,237 A | 10/1973 | Chia et al. |
| 3,766,241 A | 10/1973 | Drinkard, Jr. et al. |
| 3,773,809 A | 11/1973 | Walter |
| 3,775,461 A | 11/1973 | Drinkard, Jr. et al. |
| 3,798,256 A | 3/1974 | King et al. |
| 3,818,067 A | 6/1974 | Downing et al. |
| 3,818,068 A | 6/1974 | Wells |
| 3,846,474 A | 11/1974 | Mok |
| 3,849,472 A | 11/1974 | Waddan |
| 3,850,973 A | 11/1974 | Seidel et al. |
| 3,853,754 A | 12/1974 | Gosser |
| 3,853,948 A | 12/1974 | Drinkard, Jr. et al. |
| 3,864,380 A | 2/1975 | King et al. |
| 3,869,501 A | 3/1975 | Waddan |
| 3,920,721 A | 11/1975 | Gosser |
| 3,927,056 A | 12/1975 | Gosser |
| 3,947,487 A | 3/1976 | Crooks |
| 4,045,495 A | 8/1977 | Nazarenko et al. |
| 4,046,815 A | 9/1977 | Nazarenko |
| 4,076,756 A | 2/1978 | Nazarenko et al. |
| 4,087,452 A | 5/1978 | Kuntz |
| 4,146,555 A | 3/1979 | Kershaw |
| 4,147,717 A | 4/1979 | Kershaw |
| 4,177,215 A | 12/1979 | Seidel |
| 4,210,558 A | 7/1980 | Crooks |
| 4,211,725 A | 7/1980 | Kluger et al. |
| 4,230,634 A | 10/1980 | Benzie et al. |
| 4,240,976 A | 12/1980 | Benzie et al. |
| 4,251,468 A | 2/1981 | Nazarenko |
| 4,260,556 A | 4/1981 | Kluger et al. |
| 4,328,172 A | 5/1982 | Rapoport |
| 4,330,483 A | 5/1982 | Rapoport |
| 4,339,395 A | 7/1982 | Barnette et al. |
| 4,371,474 A | 2/1983 | Rapoport |
| 4,382,038 A | 5/1983 | McGill |
| 4,385,007 A | 5/1983 | Shook, Jr. |
| 4,416,824 A | 11/1983 | Reimer et al. |
| 4,416,825 A | 11/1983 | Ostermaier |
| 4,434,316 A | 2/1984 | Barnette |
| 4,496,474 A | 1/1985 | Reck |
| 4,539,302 A | 9/1985 | Leyendecker et al. |
| 4,705,881 A | 11/1987 | Rapoport |
| 4,749,801 A | 6/1988 | Bealty et al. |
| 4,774,353 A | 9/1988 | Hall et al. |
| 4,874,884 A | 10/1989 | McKinney et al. |
| 4,990,645 A | 2/1991 | Back et al. |
| 5,070,202 A | 12/1991 | Herkes |
| 5,107,012 A | 4/1992 | Grunewald |
| 5,302,756 A | 4/1994 | McKinney |

(Continued)

FOREIGN PATENT DOCUMENTS

AU    6522096    2/1997

(Continued)

OTHER PUBLICATIONS

U.S. Appl. No. 08/379,429.

(Continued)

*Primary Examiner* — Kamal A Saeed
(74) *Attorney, Agent, or Firm* — Robert B. Furr, Jr.

(57) ABSTRACT

A process for making 3-aminopentanenitrile from a crude 2-pentenenitrile ("crude 2PN") comprising 2-pentenenitrile, 2-methyl-2-butenenitrile, and 2-methyl-3-butenenitrile includes contacting the crude 2PN with an ammonia-containing fluid and water. The ammonia-containing fluid can include at least one reactant selected from the group consisting of ammonia, aqueous ammonia, and ammonium hydroxide.

10 Claims, No Drawings

U.S. PATENT DOCUMENTS

| | | |
|---|---|---|
| 5,312,959 A | 5/1994 | Sieja et al. |
| 5,449,807 A | 9/1995 | Druliner |
| 5,488,129 A | 1/1996 | Huser et al. |
| 5,512,695 A | 4/1996 | Kreutzer et al. |
| 5,512,696 A | 4/1996 | Kreutzer et al. |
| 5,523,453 A | 6/1996 | Breikss |
| 5,543,536 A | 8/1996 | Tam |
| 5,663,369 A | 9/1997 | Kreutzer et al. |
| 5,688,986 A | 11/1997 | Tam et al. |
| 5,696,280 A | 12/1997 | Shapiro |
| 5,709,841 A | 1/1998 | Reimer |
| 5,723,641 A | 3/1998 | Tam et al. |
| 5,773,637 A | 6/1998 | Cicha et al. |
| 5,821,378 A | 10/1998 | Foo et al. |
| 5,847,191 A | 12/1998 | Bunel et al. |
| 5,856,555 A | 1/1999 | Huser et al. |
| 5,902,883 A | 5/1999 | Herkes |
| 5,908,805 A | 6/1999 | Huser et al. |
| 5,959,135 A | 9/1999 | Garner et al. |
| 6,090,987 A | 7/2000 | Billig et al. |
| 6,121,184 A | 9/2000 | Druliner et al. |
| 6,147,247 A | 11/2000 | Voit et al. |
| 6,169,198 B1 | 1/2001 | Fischer et al. |
| 6,171,996 B1 | 1/2001 | Garner et al. |
| 6,197,992 B1 | 3/2001 | Fischer et al. |
| 6,242,633 B1 | 6/2001 | Fischer et al. |
| 6,284,865 B1 | 9/2001 | Tam et al. |
| 6,307,109 B1 | 10/2001 | Kanel et al. |
| 6,355,833 B2 | 3/2002 | Fischer et al. |
| 6,461,481 B1 | 10/2002 | Barnette et al. |
| 6,469,194 B2 | 10/2002 | Burattin et al. |
| 6,521,778 B1 | 2/2003 | Fischer et al. |
| 6,646,148 B1 | 11/2003 | Kreutzer |
| 6,660,877 B2 | 12/2003 | Lenges et al. |
| 6,737,539 B2 | 5/2004 | Lenges et al. |
| 6,753,440 B2 | 6/2004 | Druliner et al. |
| 6,770,770 B1 | 8/2004 | Baumann et al. |
| 6,846,945 B2 | 1/2005 | Lenges et al. |
| 6,852,199 B2 | 2/2005 | Jungkamp et al. |
| 6,855,799 B2 | 2/2005 | Tam et al. |
| 6,897,329 B2 | 5/2005 | Jackson et al. |
| 6,984,604 B2 | 1/2006 | Cobb et al. |
| 7,022,866 B2 | 4/2006 | Bartsch et al. |
| 7,067,685 B2 | 6/2006 | Bartsch et al. |
| 7,084,293 B2 | 8/2006 | Rosier et al. |
| 7,084,294 B2 | 8/2006 | Jungkamp et al. |
| 7,098,358 B2 | 8/2006 | Burattin et al. |
| 7,105,696 B2 | 9/2006 | Burattin et al. |
| 7,253,298 B2 | 8/2007 | Galland et al. |
| 7,345,006 B2 | 3/2008 | Bartsch et al. |
| 7,381,845 B2 | 6/2008 | Weiskopf et al. |
| 7,439,381 B2 | 10/2008 | Jungkamp et al. |
| 7,442,825 B2 | 10/2008 | Galland et al. |
| 7,470,805 B2 | 12/2008 | Rosier et al. |
| 7,521,575 B2 | 4/2009 | Bartsch et al. |
| 7,528,275 B2 | 5/2009 | Bartsch et al. |
| 7,538,240 B2 | 5/2009 | Jungkamp et al. |
| 7,541,486 B2 | 6/2009 | Scheidel et al. |
| 7,700,795 B2 | 4/2010 | Haderlein et al. |
| 2001/0014647 A1 | 8/2001 | Fischer et al. |
| 2001/0049431 A1 | 12/2001 | Tam et al. |
| 2003/0045740 A1 | 3/2003 | Druliner et al. |
| 2003/0135014 A1 | 7/2003 | Radu et al. |
| 2003/0212298 A1 | 11/2003 | Brasse et al. |
| 2004/0012225 A1 | 1/2004 | Schlecht et al. |
| 2004/0063956 A1 | 4/2004 | Burattin et al. |
| 2004/0063991 A1 | 4/2004 | Burattin et al. |
| 2004/0176622 A1 | 9/2004 | Bartsch et al. |
| 2004/0235648 A1 | 11/2004 | Bartsch et al. |
| 2004/0260112 A1 | 12/2004 | Basset et al. |
| 2005/0090677 A1 | 4/2005 | Bartsch et al. |
| 2005/0090678 A1 | 4/2005 | Bartsch et al. |
| 2005/0247624 A1 | 11/2005 | Jungkamp et al. |
| 2006/0142609 A1 | 6/2006 | Bourgeois et al. |
| 2006/0175189 A1 | 8/2006 | Gerber et al. |
| 2006/0252955 A1 | 11/2006 | Rosier et al. |
| 2006/0258873 A1 | 11/2006 | Rosier et al. |
| 2006/0258874 A1 | 11/2006 | Bartsch et al. |
| 2006/0264651 A1 | 11/2006 | Bartsch et al. |
| 2007/0060766 A1 | 3/2007 | Bartsch et al. |
| 2007/0073071 A1 | 3/2007 | Haderlein et al. |
| 2007/0083057 A1 | 4/2007 | Haderlein et al. |
| 2007/0088173 A1 | 4/2007 | Haderlein et al. |
| 2007/0112215 A1 | 5/2007 | Jungkamp et al. |
| 2007/0155977 A1 | 7/2007 | Jungkamp et al. |
| 2007/0155978 A1 | 7/2007 | Jungkamp et al. |
| 2007/0155980 A1 | 7/2007 | Scheidel et al. |
| 2008/0015378 A1 | 1/2008 | Foo et al. |
| 2008/0015380 A1 | 1/2008 | Foo et al. |
| 2008/0015381 A1 | 1/2008 | Foo et al. |
| 2008/0015382 A1 | 1/2008 | Foo et al. |
| 2008/0071105 A1 | 3/2008 | Bartsch et al. |
| 2008/0076944 A1 | 3/2008 | Bartsch et al. |
| 2008/0083607 A1 | 4/2008 | Deckert et al. |
| 2008/0221351 A1 | 9/2008 | Bartsch et al. |
| 2008/0227214 A1 | 9/2008 | Jungkamp et al. |
| 2008/0227998 A1 | 9/2008 | Scheidel et al. |
| 2008/0242883 A1 | 10/2008 | Jungkamp et al. |
| 2008/0242885 A1 | 10/2008 | Jungkamp et al. |
| 2008/0242886 A1 | 10/2008 | Bartsch et al. |
| 2008/0275266 A1 | 11/2008 | Bartsch et al. |
| 2008/0281119 A1 | 11/2008 | Scheidel et al. |
| 2008/0281120 A1 | 11/2008 | Jungkamp et al. |
| 2009/0054671 A1 | 2/2009 | Haderlein et al. |

FOREIGN PATENT DOCUMENTS

| | | |
|---|---|---|
| AU | 199665220 A | 2/1997 |
| CA | 1324613 C | 11/1993 |
| CA | 2462720 A1 | 4/2003 |
| CA | 2552862 A1 | 8/2005 |
| CN | 1113854 A | 12/1995 |
| CN | 1145531 A | 3/1997 |
| CN | 1146166 A | 3/1997 |
| CN | 1146762 A | 4/1997 |
| CN | 1159106 A | 9/1997 |
| CN | 1159799 A | 9/1997 |
| CN | 1163606 A | 10/1997 |
| CN | 1169143 A | 12/1997 |
| CN | 1173935 A | 2/1998 |
| CN | 1179147 A | 4/1998 |
| CN | 1198151 A | 11/1998 |
| CN | 1204111 A | 1/1999 |
| CN | 1206357 A | 1/1999 |
| CN | 1211931 A | 3/1999 |
| CN | 1045591 C | 10/1999 |
| CN | 1236355 A | 11/1999 |
| CN | 1047163 C | 12/1999 |
| CN | 1245489 A | 2/2000 |
| CN | 1247102 A | 3/2000 |
| CN | 1052718 C | 5/2000 |
| CN | 1265094 A | 8/2000 |
| CN | 1266424 A | 9/2000 |
| CN | 1270543 A | 10/2000 |
| CN | 1068307 C | 7/2001 |
| CN | 1304334 A | 7/2001 |
| CN | 1069310 C | 8/2001 |
| CN | 1072980 C | 10/2001 |
| CN | 1076342 C | 12/2001 |
| CN | 1327881 A | 12/2001 |
| CN | 1331843 A | 1/2002 |
| CN | 1333745 A | 1/2002 |
| CN | 1082946 C | 4/2002 |
| CN | 1344180 A | 4/2002 |
| CN | 1356335 A | 7/2002 |
| CN | 1387534 A | 12/2002 |
| CN | 1099912 C | 1/2003 |
| CN | 1390241 A | 1/2003 |
| CN | 1103613 C | 3/2003 |
| CN | 1106218 C | 4/2003 |
| CN | 1108643 C | 5/2003 |
| CN | 1427807 A | 7/2003 |
| CN | 1449400 A | 10/2003 |
| CN | 1461295 A | 12/2003 |
| CN | 1471510 A | 1/2004 |
| CN | 1141285 C | 3/2004 |
| CN | 1142224 C | 3/2004 |
| CN | 1144781 C | 4/2004 |

| | | | | | | | |
|---|---|---|---|---|---|---|---|
| CN | 1487917 | A | 4/2004 | EP | 464691 | B1 | 12/1993 |
| CN | 1152855 | C | 6/2004 | EP | 675871 | B1 | 4/1997 |
| CN | 1535179 | A | 10/2004 | EP | 634395 | B1 | 9/1997 |
| CN | 1564807 | A | 1/2005 | EP | 650959 | B1 | 9/1997 |
| CN | 1568225 | A | 1/2005 | EP | 784610 | B1 | 2/1999 |
| CN | 1568226 | A | 1/2005 | EP | 757672 | B1 | 6/1999 |
| CN | 1617892 | A | 5/2005 | EP | 792259 | B1 | 8/1999 |
| CN | 1617900 | A | 5/2005 | EP | 804412 | B1 | 12/1999 |
| CN | 1212293 | C | 7/2005 | EP | 1000019 | A1 | 5/2000 |
| CN | 1639176 | A | 7/2005 | EP | 1001928 | A1 | 5/2000 |
| CN | 1213051 | C | 8/2005 | EP | 1003716 | A1 | 5/2000 |
| CN | 1665776 | A | 9/2005 | EP | 1019190 | A1 | 7/2000 |
| CN | 1670139 | A | 9/2005 | EP | 755302 | B1 | 10/2000 |
| CN | 1674989 | A | 9/2005 | EP | 929513 | B1 | 4/2001 |
| CN | 1675172 | A | 9/2005 | EP | 881924 | B1 | 5/2001 |
| CN | 1222358 | C | 10/2005 | EP | 854858 | B1 | 6/2001 |
| CN | 1732148 | A | 2/2006 | EP | 815073 | B1 | 7/2001 |
| CN | 1735460 | A | 2/2006 | EP | 1144114 | A3 | 9/2001 |
| CN | 1245489 | C | 3/2006 | EP | 1091804 | B1 | 2/2002 |
| CN | 1740183 | A | 3/2006 | EP | 944585 | B1 | 4/2002 |
| CN | 1745062 | A | 3/2006 | EP | 1000019 | B1 | 2/2003 |
| CN | 1767895 | A | 5/2006 | EP | 911339 | B1 | 4/2003 |
| CN | 1260009 | C | 6/2006 | EP | 1216268 | B1 | 11/2003 |
| CN | 1266424 | C | 7/2006 | EP | 1350788 | A3 | 11/2003 |
| CN | 1270543 | C | 8/2006 | EP | 1003607 | B1 | 12/2003 |
| CN | 1274671 | C | 9/2006 | EP | 1003716 | B1 | 2/2004 |
| CN | 1274699 | C | 9/2006 | EP | 1313743 | B1 | 3/2004 |
| CN | 1835915 | A | 9/2006 | EP | 1414567 | A1 | 5/2004 |
| CN | 1279088 | C | 10/2006 | EP | 1427695 | A1 | 6/2004 |
| CN | 1847288 | A | 10/2006 | EP | 1438133 | A1 | 7/2004 |
| CN | 1283620 | C | 11/2006 | EP | 1019190 | B1 | 12/2004 |
| CN | 1857775 | A | 11/2006 | EP | 1140801 | B1 | 2/2005 |
| CN | 1289539 | C | 12/2006 | EP | 1395547 | B1 | 3/2005 |
| CN | 1293942 | C | 1/2007 | EP | 1001928 | B1 | 4/2005 |
| CN | 1906150 | A | 1/2007 | EP | 1521736 | A1 | 4/2005 |
| CN | 1914154 | A | 2/2007 | EP | 1521737 | A1 | 4/2005 |
| CN | 1914155 | A | 2/2007 | EP | 1521738 | A2 | 4/2005 |
| CN | 1914156 | A | 2/2007 | EP | 1603865 | A1 | 12/2005 |
| CN | 1914157 | A | 2/2007 | EP | 1324976 | B1 | 2/2006 |
| CN | 1914158 | A | 2/2007 | EP | 1214975 | B1 | 3/2006 |
| CN | 1914159 | A | 2/2007 | EP | 1324978 | B1 | 3/2006 |
| CN | 1914160 | A | 2/2007 | EP | 1648860 | A1 | 4/2006 |
| CN | 1914161 | A | 2/2007 | EP | 891323 | B1 | 6/2006 |
| CN | 1914162 | A | 2/2007 | EP | 1226147 | B1 | 6/2006 |
| CN | 1914165 | A | 2/2007 | EP | 1438317 | B1 | 6/2006 |
| CN | 1914166 | A | 2/2007 | EP | 1682561 | A1 | 7/2006 |
| CN | 1914167 | A | 2/2007 | EP | 1448668 | B1 | 8/2006 |
| CN | 1914216 | A | 2/2007 | EP | 1587621 | B1 | 8/2006 |
| CN | 1307237 | C | 3/2007 | EP | 1713759 | A1 | 10/2006 |
| CN | 1315790 | C | 5/2007 | EP | 1713761 | A1 | 10/2006 |
| CN | 1318432 | C | 5/2007 | EP | 1713762 | A1 | 10/2006 |
| CN | 1997624 | A | 7/2007 | EP | 1713766 | A1 | 10/2006 |
| CN | 1331843 | C | 8/2007 | EP | 1716102 | A2 | 11/2006 |
| CN | 101020641 | A | 8/2007 | EP | 1716103 | A1 | 11/2006 |
| CN | 101035799 | A | 9/2007 | EP | 1716104 | A1 | 11/2006 |
| CN | 101043946 | A | 9/2007 | EP | 1716105 | A1 | 11/2006 |
| CN | 100348322 | C | 11/2007 | EP | 1716106 | A1 | 11/2006 |
| CN | 100351227 | C | 11/2007 | EP | 1716107 | A1 | 11/2006 |
| CN | 100352824 | C | 12/2007 | EP | 1716109 | A2 | 11/2006 |
| CN | 100361966 | C | 1/2008 | EP | 1610893 | B1 | 3/2007 |
| CN | 100364666 | C | 1/2008 | EP | 1621531 | B1 | 3/2007 |
| DE | 1807088 | U | 3/1960 | EP | 1438132 | B1 | 4/2007 |
| DE | 1807088 | A1 | 6/1969 | EP | 1799697 | A1 | 6/2007 |
| DE | 2055747 | A1 | 5/1971 | EP | 1713764 | B1 | 8/2007 |
| DE | 1593277 | B2 | 8/1973 | EP | 1713816 | B1 | 8/2007 |
| DE | 1593277 | C3 | 3/1974 | EP | 1825914 | A1 | 8/2007 |
| DE | 2700904 | C2 | 10/1983 | EP | 1448620 | B1 | 6/2008 |
| DE | 68909466 | T2 | 3/1994 | EP | 1817108 | B1 | 6/2008 |
| DE | 10136488 | A1 | 2/2003 | EP | 1713760 | B1 | 7/2008 |
| DE | 10150285 | A1 | 4/2003 | EP | 1571172 | B1 | 10/2008 |
| DE | 10350999 | A1 | 6/2005 | EP | 1988998 | A1 | 11/2008 |
| DE | 102004004696 | A1 | 8/2005 | EP | 1265832 | B1 | 5/2009 |
| EP | 0001899 | B1 | 3/1982 | EP | 1592659 | B1 | 7/2009 |
| EP | 123438 | B1 | 7/1987 | EP | 1586598 | B1 | 9/2009 |
| EP | 160296 | B1 | 10/1988 | EP | 2098106 | A1 | 9/2009 |
| EP | 268448 | B1 | 9/1991 | EP | 1567478 | B1 | 10/2009 |
| EP | 510689 | A1 | 10/1992 | EP | 1682559 | B1 | 12/2009 |
| EP | 248643 | B1 | 3/1993 | EP | 1630166 | B1 | 2/2010 |
| EP | 336314 | B1 | 9/1993 | FR | 1544656 | A | 11/1968 |

| | | | | | | |
|---|---|---|---|---|---|---|
| FR | 2015115 | A5 | 4/1970 | JP | 10509954 A | 9/1998 |
| FR | 1603513 | A | 5/1971 | JP | 02818503 B2 | 10/1998 |
| FR | 2069411 | A5 | 9/1971 | JP | 10512879 A | 12/1998 |
| FR | 2845379 | B1 | 12/2004 | JP | 11501660 A | 2/1999 |
| FR | 2873696 | A1 | 2/2006 | JP | 11504262 A | 4/1999 |
| FR | 2873696 | B1 | 10/2006 | JP | 02911608 B2 | 6/1999 |
| GB | 0219474 | | 7/1924 | JP | 11507297 A | 6/1999 |
| GB | 1104140 | A | 2/1968 | JP | 03001298 B2 | 1/2000 |
| GB | 1203702 | A | 9/1970 | JP | 03069915 B2 | 7/2000 |
| GB | 1213175 | A | 11/1970 | JP | 2001500135 A | 1/2001 |
| GB | 1429169 | A | 3/1976 | JP | 2001506250 A | 5/2001 |
| GB | 1429621 | A | 3/1976 | JP | 2001512097 A | 8/2001 |
| GB | 1436932 | A | 5/1976 | JP | 03205587 B2 | 9/2001 |
| GB | 1458322 | A | 12/1976 | JP | 2001516640 A | 10/2001 |
| GB | 1482909 | A | 8/1977 | JP | 03285878 B2 | 5/2002 |
| GB | 2007521 | A | 5/1979 | JP | 2002517473 A | 6/2002 |
| GB | 1565443 | A | 4/1980 | JP | 03320424 B2 | 9/2002 |
| GB | 1594694 | A | 8/1981 | JP | 2002533321 A | 10/2002 |
| GB | 2007521 | B | 6/1982 | JP | 03380543 B2 | 2/2003 |
| HK | 1025950 | A1 | 7/2003 | JP | 2003510385 A | 3/2003 |
| HK | 1026383 | A1 | 7/2004 | JP | 2003526688 A | 9/2003 |
| HK | 1052364 | A1 | 5/2007 | JP | 03478399 B2 | 12/2003 |
| JP | 48028423 | Y1 | 8/1973 | JP | 2004501058 A | 1/2004 |
| JP | 48028423 | B | 9/1973 | JP | 2004507550 A | 3/2004 |
| JP | 49043924 | Y1 | 12/1974 | JP | 03519410 B2 | 4/2004 |
| JP | 50059324 | U | 6/1975 | JP | 03535172 B2 | 6/2004 |
| JP | 50059326 | U | 6/1975 | JP | 03553952 B2 | 8/2004 |
| JP | 51007649 | B | 3/1976 | JP | 2004534032 A | 11/2004 |
| JP | 52012698 | B | 4/1977 | JP | 2004535929 A | 12/2004 |
| JP | 1013127 | C | 9/1980 | JP | 03621133 B2 | 2/2005 |
| JP | 55047031 | B | 11/1980 | JP | 2005503410 A | 2/2005 |
| JP | 57156454 | U | 10/1982 | JP | 2005505610 A | 2/2005 |
| JP | 57156455 | U | 10/1982 | JP | 2005505611 A | 2/2005 |
| JP | 57179144 | U | 11/1982 | JP | 2005510588 A | 4/2005 |
| JP | 1136333 | C | 2/1983 | JP | 2005510605 A | 4/2005 |
| JP | 58067658 | U | 5/1983 | JP | 2004509942 | 10/2005 |
| JP | 58126892 | U | 8/1983 | JP | 2005533095 A | 11/2005 |
| JP | 1170710 | C | 10/1983 | JP | 2005533096 A | 11/2005 |
| JP | 58159452 | U | 10/1983 | JP | 2005538075 A | 12/2005 |
| JP | 60044295 | A | 3/1985 | JP | 03739404 B2 | 1/2006 |
| JP | 60044295 | B | 10/1985 | JP | 2004534032 | 1/2006 |
| JP | 62294691 | A | 12/1987 | JP | 2004535929 | 1/2006 |
| JP | 63135363 | U | 9/1988 | JP | 2006000451 A | 1/2006 |
| JP | 1013127 | Y2 | 4/1989 | JP | 2006511591 A | 4/2006 |
| JP | 1209830 | A | 8/1989 | JP | 2006519797 A | 8/2006 |
| JP | 1136333 | U | 9/1989 | JP | 2006528616 A | 12/2006 |
| JP | 1050220 | B | 10/1989 | JP | 2007083057 A | 4/2007 |
| JP | 1173751 | U | 12/1989 | JP | 2007509885 A | 4/2007 |
| JP | 1565159 | C | 6/1990 | JP | 2007509886 A | 4/2007 |
| JP | 3001298 | B | 1/1991 | JP | 2007509887 A | 4/2007 |
| JP | 1615749 | C | 8/1991 | JP | 2007519516 A | 7/2007 |
| JP | 3205587 | A | 9/1991 | JP | 2007519663 A | 7/2007 |
| JP | 1627124 | C | 11/1991 | JP | 2007519664 A | 7/2007 |
| JP | 1627146 | C | 11/1991 | JP | 2007519666 A | 7/2007 |
| JP | 3069915 | B | 11/1991 | JP | 2007519667 A | 7/2007 |
| JP | 3285878 | A | 12/1991 | JP | 2007519670 A | 7/2007 |
| JP | 1642102 | C | 2/1992 | JP | 2007519671 A | 7/2007 |
| JP | 4012248 | Y2 | 3/1992 | JP | 2007519672 A | 7/2007 |
| JP | 4057050 | U | 5/1992 | JP | 2007519673 A | 7/2007 |
| JP | 4166155 | A | 6/1992 | JP | 2007519674 A | 7/2007 |
| JP | 4230254 | A | 8/1992 | JP | 2007519675 A | 7/2007 |
| JP | 4057050 | B | 9/1992 | JP | 2007519677 A | 7/2007 |
| JP | 4060532 | B | 9/1992 | JP | 2007522122 A | 8/2007 |
| JP | 4118676 | U | 10/1992 | JP | 04012248 B2 | 11/2007 |
| JP | 4128141 | U | 11/1992 | JP | 2006515323 | 2/2008 |
| JP | 1729140 | C | 1/1993 | JP | 04057050 B2 | 3/2008 |
| JP | 1811422 | C | 12/1993 | JP | 04060532 B2 | 3/2008 |
| JP | 7025841 | Y2 | 6/1995 | JP | 200606512918 | 3/2008 |
| JP | 7188144 | A | 7/1995 | JP | 2008515831 A | 5/2008 |
| JP | 2037346 | C | 3/1996 | JP | 2008516907 A | 5/2008 |
| JP | 8504814 | A | 5/1996 | JP | 04118676 B2 | 7/2008 |
| JP | 8157795 | A | 6/1996 | JP | 04128141 B2 | 7/2008 |
| JP | 2098106 | C | 10/1996 | JP | 04166155 B2 | 10/2008 |
| JP | 02521777 | Y2 | 1/1997 | JP | 04230254 B2 | 2/2009 |
| JP | 02623448 | B2 | 6/1997 | KR | 198802621 Y1 | 7/1988 |
| JP | 9505586 | A | 6/1997 | KR | 198802296 B | 10/1988 |
| JP | 9512013 | A | 12/1997 | KR | 198802296 B1 | 10/1988 |
| JP | 10505101 | A | 5/1998 | KR | 199003458 B1 | 5/1990 |
| JP | 10506911 | A | 7/1998 | KR | 199008166 B1 | 11/1990 |

| | | | |
|---|---|---|---|
| KR | 199104132 B1 | 6/1991 |
| KR | 199205087 Y1 | 7/1992 |
| KR | 2006132885 A | 12/2006 |
| MX | 2004PA002764 A | 6/2004 |
| NL | 197700262 A | 7/1977 |
| NL | 188158 C | 4/1992 |
| SU | 677650 A | 7/1979 |
| TW | 387874 B | 4/2000 |
| TW | 400249 B | 8/2000 |
| TW | 453983 B | 9/2001 |
| TW | 453985 B | 9/2001 |
| TW | 455576 B | 9/2001 |
| TW | 457244 B | 10/2001 |
| TW | 458959 B | 10/2001 |
| TW | 519496 B | 2/2003 |
| TW | 527340 B | 4/2003 |
| TW | 576837 B | 2/2004 |
| TW | 580489 B | 3/2004 |
| TW | 580490 B | 3/2004 |
| TW | 584623 B | 4/2004 |
| TW | 592821 B | 6/2004 |
| TW | 226345 B | 1/2005 |
| TW | 233438 B | 6/2005 |
| TW | 245780 B | 12/2005 |
| TW | 2666650 B | 11/2006 |
| WO | WO7900193 A1 | 4/1979 |
| WO | WO9414752 A1 | 7/1994 |
| WO | WO9514659 A1 | 6/1995 |
| WO | WO9528228 A1 | 10/1995 |
| WO | WO9529153 A1 | 11/1995 |
| WO | WO9611182 A1 | 4/1996 |
| WO | WO9616022 A1 | 5/1996 |
| WO | WO9622968 A1 | 8/1996 |
| WO | WO9629303 A1 | 9/1996 |
| WO | WO9703040 A1 | 1/1997 |
| WO | WO9712857 A1 | 4/1997 |
| WO | WO9724183 A1 | 7/1997 |
| WO | WO9736855 A2 | 10/1997 |
| WO | WO9811051 A1 | 3/1998 |
| WO | WO9827054 A1 | 6/1998 |
| WO | WO9906146 A2 | 2/1999 |
| WO | WO9906356 | 2/1999 |
| WO | WO9906359 A1 | 2/1999 |
| WO | WO9913983 A1 | 3/1999 |
| WO | WO9964155 A1 | 12/1999 |
| WO | WO0001485 A2 | 1/2000 |
| WO | WO0037431 A1 | 6/2000 |
| WO | WO0121684 A1 | 3/2001 |
| WO | WO0136429 A1 | 5/2001 |
| WO | WO0168247 A2 | 9/2001 |
| WO | WO0211108 A1 | 2/2002 |
| WO | WO0213964 A2 | 2/2002 |
| WO | WO0218392 A1 | 3/2002 |
| WO | WO0226698 A1 | 4/2002 |
| WO | WO0230854 A2 | 4/2002 |
| WO | WO02053527 A1 | 7/2002 |
| WO | WO02092551 A2 | 11/2002 |
| WO | WO03011457 A1 | 2/2003 |
| WO | WO03018540 A1 | 3/2003 |
| WO | WO03024919 A1 | 3/2003 |
| WO | WO03031392 A1 | 4/2003 |
| WO | WO03033141 A1 | 4/2003 |
| WO | WO03033509 A1 | 4/2003 |
| WO | WO03046019 A1 | 6/2003 |
| WO | WO03046049 A1 | 6/2003 |
| WO | WO03068729 A1 | 8/2003 |
| WO | WO03076394 A1 | 9/2003 |
| WO | WO2004007431 A1 | 1/2004 |
| WO | WO2004007432 A1 | 1/2004 |
| WO | WO2004007435 A2 | 1/2004 |
| WO | WO2004007508 A2 | 1/2004 |
| WO | WO0168247 A8 | 6/2004 |
| WO | WO2004060855 A1 | 7/2004 |
| WO | WO2004064994 A2 | 8/2004 |
| WO | WO2004065352 A2 | 8/2004 |
| WO | WO2004080924 A2 | 9/2004 |
| WO | WO2004080948 A1 | 9/2004 |
| WO | WO2004087314 A1 | 10/2004 |
| WO | WO2005019160 A1 | 3/2005 |
| WO | WO2005042156 A1 | 5/2005 |
| WO | WO2005042157 A2 | 5/2005 |
| WO | WO2005042547 A1 | 5/2005 |
| WO | WO2005042549 A1 | 5/2005 |
| WO | WO2005073167 A1 | 8/2005 |
| WO | WO2005073168 A1 | 8/2005 |
| WO | WO2005073169 A1 | 8/2005 |
| WO | WO2005073170 A1 | 8/2005 |
| WO | WO2005073171 A1 | 8/2005 |
| WO | WO2005073172 A1 | 8/2005 |
| WO | WO2005073173 A1 | 8/2005 |
| WO | WO2005073174 A1 | 8/2005 |
| WO | WO2005073175 A1 | 8/2005 |
| WO | WO2005073176 A1 | 8/2005 |
| WO | WO2005073178 A2 | 8/2005 |
| WO | WO2005073179 A1 | 8/2005 |
| WO | WO2005073241 A1 | 8/2005 |
| WO | WO2006040023 A1 | 4/2006 |
| WO | WO2006042675 A2 | 4/2006 |
| WO | WO2005073166 A3 | 3/2007 |
| WO | WO2007051374 A1 | 5/2007 |
| WO | WO2007096274 A1 | 8/2007 |
| WO | 2007115936 | 10/2007 |
| WO | WO2007115936 A2 | 10/2007 |
| WO | WO2008008926 A2 | 1/2008 |
| WO | WO2008008928 A2 | 1/2008 |
| WO | WO2008008929 A2 | 1/2008 |
| WO | WO2008008930 A2 | 1/2008 |
| WO | WO2008028843 A1 | 3/2008 |
| WO | WO2008062058 A1 | 5/2008 |

OTHER PUBLICATIONS

U.S. Appl. No. 09/121,105.
U.S. Appl. No. 09/157,342.
U.S. Appl. No. 09/176,241.
U.S. Appl. No. 09/198,963.
U.S. Appl. No. 09/227,802.
U.S. Appl. No. 09/320,025.
U.S. Appl. No. 09/510,074.
U.S. Appl. No. 09/679,564.
U.S. Appl. No. 09/680,947.
U.S. Appl. No. 09/680,969.
U.S. Appl. No. 09/717,909.
U.S. Appl. No. 09/874,225.
U.S. Appl. No. 09/884,548.

PROCESS OF MAKING 3-AMINOPENTANENITRILE

FIELD OF THE INVENTION

This invention relates to a process of making 3-aminopentanenitrile from 2-pentenenitrile by reacting with ammonia, aqueous ammonia, or ammonium hydroxide The invention particularly relates to a process of making 3-aminopentanenitrile from crude 2-pentenenitrile (e g, mixtures containing 2-pentenenitrile, 2-methyl-2-butenenitrile, and 2-methyl-3-butenenitrile)

BACKGROUND

3-Aminopentanenitrile is an important chemical intermediate. For example, it can be used to make 1,3-diaminopentane, which has a variety of uses including its use as an epoxy curing agent, a metal chelating agent, a chain extender for polyurethane formulations, or a monomer for forming polymers including polyamides or polyimides Other uses of 3-aminopentanenitrile include use as an intermediate in the synthesis of pharmaceuticals, as a precursor to amino-acids and amino-amides, and as an intermediate in the formation of specialty reagent chemicals U.S. Pat. Nos. 4,211,725 and 4,260,556 disclose the reaction of 2-pentenenitrile and "nucleophilic agents," such as ammonia and ethylenediamine, to produce alkylaminonitriles and dimers Such reactions take place in the presence of a metal addition catalyst U.S. Pat. No. 4,496,474 discloses the reaction of 2-pentenenitrile and alkylamines to produce the corresponding nitrile compounds U.S. Pat. No. 5,070,202 discloses the reaction of 2-pentenenitrile and an alkylamine in the presence of 15% to 60% by weight water to produce an alkylaminonitrile U.S. Pat. No. 5,902,883 discloses the cyanobutylation of ammonia, an alkylamine, or hydrazine with 3-pentenenitrile and 4-pentenenitrile and mixtures thereof to form alkylaminonitriles 3-aminopentanenitrile can, therefore, be prepared by a process of reaction of 2-pentenenitrile with ammonia, aqueous ammonia, or ammonium hydroxide The preferred raw material for this process is a purified 2-pentenenitrile, and not a crude 2-pentenenitrile (e g, a mixture containing 2-pentenenitrile, 2-methyl-2-butenenitrile, and 2-methyl-3-butenenitrile) In this regard, it was believed that significant side reactions would lead to undesirable products and reduced yield of 3-aminopentanenitrile However, it would be advantageous to use crude 2-pentenenitrile because it eliminates the need for expensive refining of the crude 2-pentenenitrile by, for example, fractional distillation under vacuum, thereby providing an overall more economical process for the manufacture of 3-aminopentanenitrile The present invention provides such a process that can use a crude 2-pentenenitrile to make 3-aminopentanenitrile

SUMMARY OF THE INVENTION

The present invention provides a process for making 3-aminopentanenitrile from a crude 2-pentenenitrile ("crude 2PN"). The process includes contacting (i) a crude 2PN, that may include 2-pentenenitrile, in combination with one or more of 2-methyl-2-butenenitrile and 2-methyl-3-butenenitrile, with (ii) an ammonia-containing fluid, and (iii) water The process involves producing a reaction mixture by using a molar excess of ammonia in the range of 10% to 20% with respect to the 2-pentenenitrile content of crude 2PN.

As used herein, the term "crude 2PN" is meant to encompass cis-2-penetenenitrile, trans 2-pentenenitrile, a mixture of cis-2-penetenenitrile and trans-2-penetenenitrile, as well as other compounds or materials commonly associated with unpurified 2-pentenenitrile raw material For example, the term crude 2PN can define a mixture comprising about 50% to about 85% cis-2-pentenenitrile; about 3% to about 25% 2-methyl-2-butenenitrile and 2-methyl-3-butenenitrile, about 0 5% to about 10% linear aliphatic mononitriles selected from, for example, 3-pentenenitrile, 4-pentenenitrile, and trans-2-pentenenitrile, and about 0 01% to about 15% hydrocarbons selected from, for example, cyclohexane and benzene.

The ammonia-containing fluid should contain at least one member selected from the group consisting of ammonia, aqueous ammonia, and ammonium hydroxide The concentration of water in the reaction mixture should be in the range of 15 wt % to 60 wt %, based on the total weight of the reaction mixture Processes falling within the scope of the invention can be carried out in continuous or batch mode and do not require a catalyst

DETAILED DESCRIPTION OF THE INVENTION

3-Aminopentanenitrile can be made from a crude 2-pentenenitrile ("crude 2PN") comprising 2-pentenenitrile, 2-methyl-2-butenenitrile, and 2-methyl-3-butenenitrile by cyanobutylation processes falling within the scope of the present invention In such processes, crude 2PN is contacted with an ammonia containing fluid and water to produce a reaction mixture. The ammonia-containing fluid can include at least one member selected from the group consisting of ammonia, aqueous ammonia, and ammonium hydroxide The reaction mixture should contain water in the range of about 15% to about 60%, such as in the range of about 25% to about 40% by weight, based on the total weight of the reaction mixture The process of the present invention can, for example, be run at a reaction temperature of about 25° C. to about 135° C., such as in the range of about 80° C. to about 110° C., either at atmospheric or autogenous pressure In addition, pressures up to about 1500 psig can be employed in the process The process can be carried out with an ammonia-containing fluid that includes at least one reagent selected from ammonia, aqueous ammonia, and ammonium hydroxide in the presence of water In one embodiment, the reaction is performed with about 19 to about 29 weight percent aqueous ammonia. An about 10% to about 20% molar excess of ammonia (i e, total at least one reagent content of the ammonia-containing fluid) relative to 2-pentenenitrile is preferred for both improved reaction rate and selectivity to the desired 3-aminopentanenitrile product Either cis- or trans-2-pentenenitrile can be employed in processes falling within the scope of the present invention Mixtures of the two isomers may also be used Mixtures of 2-pentenenitrile, 2-methyl-2-butenenitrile, and 2-methyl-3-butenenitrile may also be used in the present invention. For optimum yield of 3-aminopentanenitrile, such mixtures may contain greater than about 50% by weight of 2-pentenenitrile, such as from about 65% to about 75% by weight of 2-pentenenitrile, based on the total weight of the crude 2PN Such mixtures may also contain varying amounts of non-reactive compounds including, but not limited to, cyclohexane, benzene, and valeronitrile In this regard, a yield of 85% 3-aminopentanenitrile or greater may be achieved via processes falling within the scope of the invention In addition, processes falling within the scope of the present invention can provide for more than 90% conversion of the 2-pentenenitrile content of crude 2PN to 3-aminopentanenitrile Although processes falling within the scope of the present invention can be carried out in the absence of added solvents, it is possible to use organic solvents that are generally inert under the reaction conditions of the present invention Suitable solvents include, for example, dioxane, tetrahydrofuran, dimethylformamide, dimethylacetamide, methanol, isopropanol, and butanol Such solvents can be added to the reaction mixture separately or in conjunction with water.

The present reaction can be run batch-wise or as a continuous reaction, using water, which can be homogeneously dissolved or suspended in the liquid phase The continuous mode of operation can be run, for example, using a continuous stirred tank reactor, a trickle bed reactor, or a plug-flow reactor The 3-aminopentanenitrile formed in the present invention can be further hydrogenated to form 1,3-diaminopentane 1,3-Diaminopentane has a variety of uses including, for example, its use as an epoxy curing agent, a metal chelating agent, a chain extender for polyurethane formulations, or as a monomer for forming polymers including polyamides or polyimides

EXAMPLES

The present invention can be further illustrated in view of the following non-limiting examples

Comparative Example 1

Cyanobutylation of Aqueous Ammonia with cis-2-Pentenenitrile

A mixture of about 97 0 pounds of cis-2-pentenenitrile and about 181 0 pounds of 29% aqueous ammonia was stirred vigorously and heated at 110° C. for four hours in a 50-gallon stainless steel autoclave at an autogeneous pressure of 110 psig. Low boiling impurities were removed from the final reaction product mixture by vacuum flashing the mixture at a pressure of 610 mm Hg and at a vapor temperature of about 62° C. The isolated yield of 3-aminopentanenitrile was 90%

Example 2

Cyanobutylation of Aqueous Ammonia with a Mixture of 2-Pentenenitrile, 2-Methyl-2-butenenitrile and 2-Methyl-3-butenenitrile A mixture of approximately 70 weight percent cis-2-pentenenitrile, 14 weight percent 2-methyl-2-butenenitrile, 4 weight percent 2-methyl-3-butenenitrile, with cyclohexane, benzene, and valeronitrile making up the balance, was reacted with 29 weight percent aqueous ammonia (at 15 percent molar excess relative to cis-2-pentenenitrile) in a stirred batch reactor at about 90° to 100° C., at an autogeneous pressure of about 60 to 118 psig, for approximately ten hours Vacuum distillation of the crude reaction mixture to remove low boiling impurities and water resulted in 91% selectivity to 3-aminopentanenitrile at 97% conversion of the starting cis-2-pentenenitrile

The invention claimed is:

1. A process for making 3-aminopentanenitrile, comprising (a) contacting (i) a crude 2-pentenenitrile ("crude 2PN") that may include 2-pentenenitrile in combination with one or more of 2-methyl-2-butenenitrile and 2-methyl-3-butenenitrile, with (ii) an ammonia-containing fluid, and (iii) water, using a molar excess of ammonia with respect to 2-pentenenitrile content of crude 2PN in the range of 10% to 20%, to produce a reaction mixture,
wherein
the 2-penetenenitrile is cis-2-penetenenitrile, trans-2-penetenenitrile, or a mixture of cis-2-penetenenitrile and trans-2-penetenenitrile, and
the ammonia-containing fluid comprises at least one member selected from the group consisting of ammonia, aqueous ammonia, and ammonium hydroxide, and
(b) maintaining the concentration of water in the reaction mixture in the range of 15 wt % to 60 wt %, based on the total weight of the reaction mixture.

2. The process of claim 1, wherein the ammonia-containing fluid comprises aqueous ammonia comprising 19 wt % to 29 wt % ammonia.

3. The process of claim 1, wherein the molar excess of ammonia with respect to 2-pentenenitrile content of crude 2PN is 15%.

4. The process of claim 1, wherein the process is carried out in a reactor at a temperature in the range of 25° C. to 135° C., preferably 80° C. to 110° C., and at a pressure in the range of atmospheric pressure to 1500 psig.

5. The process of claim 1, wherein the crude 2PN comprises greater than 50 wt % 2-pentenenitrile, preferably 65 wt % to 75 wt % 2-pentenenitrile, based on the total weight of the crude 2PN.

6. The process of claim 1, wherein the concentration of water in the reaction mixture is maintained in the range of 25 wt % to 40 wt %, based on the total weight of the reaction mixture.

7. The process of claim 1, wherein the reaction mixture further includes at least one added solvent selected from the group consisting of dioxane, tetrahydrofuran, dimethylformamide, dimethylacetamide, methanol, isopropanol, and butanol.

8. The process of claim 1, further comprising (c) boiling off impurities to isolate 3-aminopentanenitrile.

9. The process of claim 8 wherein yield of 3-aminopentanenitrile is 85% or greater.

10. The process of claim 8, wherein greater than 90% of the 2-pentenenitrile content of crude 2PN is converted to 3-aminopentanenitrile.

* * * * *